US005300519A

United States Patent [19]

Jones et al.

[11] Patent Number: 5,300,519

[45] Date of Patent: Apr. 5, 1994

[54] IMMUNOSUPPRESSIVE AGENTS

[75] Inventors: David N. Jones; John L. Maddocks, both of Sheffield, United Kingdom

[73] Assignee: The University of Sheffield, Sheffield, United Kingdom

[21] Appl. No.: 20,162

[22] PCT Filed: Jul. 6, 1989

[86] PCT No.: PCT/GB89/00771

§ 371 Date: Mar. 6, 1991

§ 102(e) Date: Mar. 6, 1991

[87] PCT Pub. No.: WO90/00549

PCT Pub. Date: Jan. 25, 1990

Related U.S. Application Data

[63] Continuation of Ser. No. 915,784, Jul. 16, 1992, abandoned, which is a continuation of Ser. No. 663,873, Mar. 6, 1991, abandoned.

[30] Foreign Application Priority Data

Jun. 12, 1991 [GB] United Kingdom ................ 8816123

[51] Int. Cl.[5] .................... A61K 31/415; A61K 31/41

[52] U.S. Cl. .................................... 514/363; 514/365; 514/381; 514/383

[58] Field of Search ............... 514/340, 383, 381, 365, 514/363

[56] References Cited

PUBLICATIONS

Chan et al., "Chemical Abstract" 107(13), 1987 #111843Z.

Startford et al., "Chemical Abstract" 102(19), 1985 #163025a.

Van Caneghem et al. Chemical Abstract, 105(3), #21069f, 1986.

*Primary Examiner*—Mukund J. Shah
*Assistant Examiner*—Y. N. Gupta
*Attorney, Agent, or Firm*—Salter, Michaelson & Benson

[57] ABSTRACT

A compound with immunosuppressive properties having formula (I), in which $R^1$ represents a heterocyclic ring system, a combined heterocyclic ring system and homocyclic ring system, or an ethoxycarbonylmethyl group. $R^2$ and $R^3$ represent hydrogen or lower alkyl groups.

4 Claims, No Drawings

IMMUNOSUPPRESSIVE AGENTS

This is a continuation of Application Ser. No. 07/915,784 filed on Jul. 16, 1992, which is a continuation of application Ser. No. 07/663,873 filed Mar. 6, 1991 both abandoned.

This invention relates to immunosuppressive agents.

The purine derivative azathioprine interfers with cell replication, and has immunosuppressive and antileukamic properties. It is used extensively as a drug to treat a wide range of chronic inflammatory diseases in which immune mechanisms are involved such as rheumatoid arthritis; chronic active hepatitis; kidney disease; skin disease; and multiple sclerosis. It is also used to inhibit the rejection of transplanted organs such as kidneys. However, its beneficial therapeutic effects are compromised by the fact that it is toxic to bone marrow. It is the object of the present invention to provide an immunosuppressive agent which does not have this disadvantage.

According to one aspect of the invention there is provided a compound for use as an immunosuppressive agent, said compound having the formula:

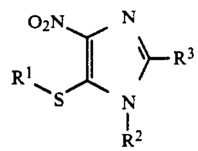

in which $R^1$ comprises a heterocyclic ring system, a homocyclic ring system, a combined heterocyclic and homocyclic ring system, alkoxycarbonylalkyl or aryloxycarbonylalkyl group and wherein $R^1$ does nòt comprise

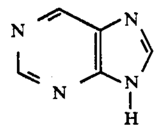

or isomers thereof.

$R^1$ is alkyl, aryl or hydrogen and $R^3$ is hydrogen, alkyl, aryl or nitroaryl Preferably $R^2$ is hydrogen, methyl, ethyl, or propyl; and $R^3$ is hydrogen, methyl or 4-nitrophenyl.

According to a preferred embodiment of the invention said compounds which are used as immunosuppressive agents have the following formula:

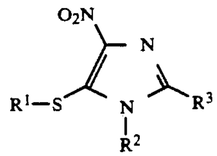

in which $R^2$ is hydrogen, or methyl or ethyl or propyl; and $R^3$ is hydrogen or methyl or 4-nitrophenyl, and in which $R^1$ may be one of the following:

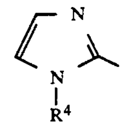

in which $R^4$ is hydrogen or methyl or ethyl or propyl or phenyl or 1-naphthyl 2.

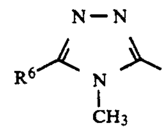

in which $R^5$ is hydrogen or trifluoromethyl or phenyl or 4-chlorophenyl or 4-methoxyphenyl or 3-pyridyl 3.

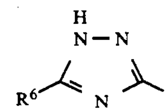

in which $R^6$ hydrogen or phenyl or chlorophenyl or 4-methoxyphenyl 4.

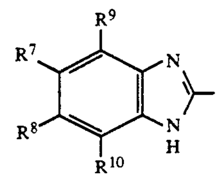

in which $R^{10}$ is hydrogen or an alkoxy group; and $R^7$ is hydrogen, alkyl, nitro, halide or an alkoxy group; and $R^8$ is hydrogen, halide or an alkoxy group; and $R^9$ is hydrogen or an alkoxy group 5.

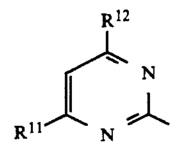

in which $R^{11}$ is hydrogen, methyl, or hydroxyl; and $R^{12}$ is hydrogen or methyl; and X is nitrogen or C—H 6.

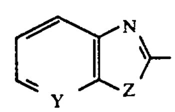

in which

Z is oxygen or sulphur or N—H; and

Y is C—H or nitrogen 7.

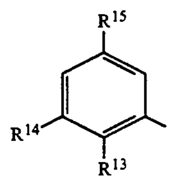
in which
$R^{13}$ is hydrogen or an amino or carboxyl group; and
$R^{14}$ is hydrogen or methyl; and
$R^{15}$ is hydrogen or methyl 8.
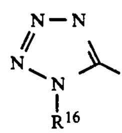
in which
$R^{16}$ is alkyl or aryl 9.
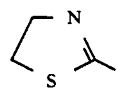
10.
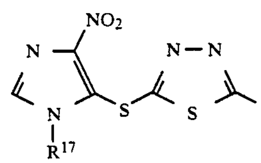
in which
$R^{17}$ is alkyl or aryl 11.
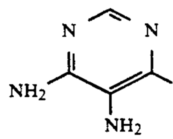
12.
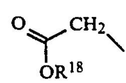
in which $R^{18}$ is alkyl or aryl 13.
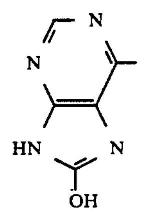
Specific illustrative examples of the first embodiment of the invention are as follows:
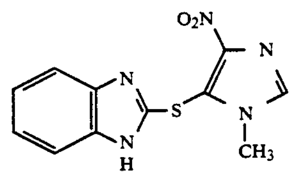
(1)
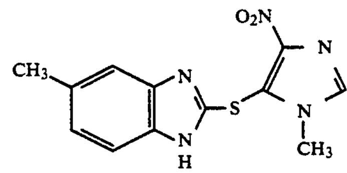
(2)
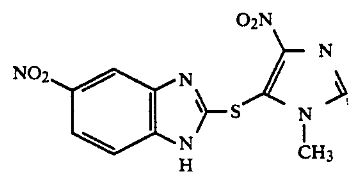
(3)
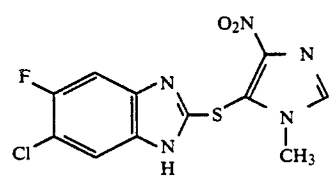
(4)
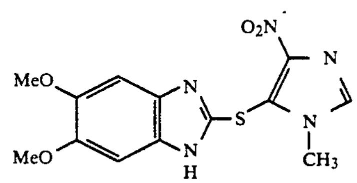
(5)
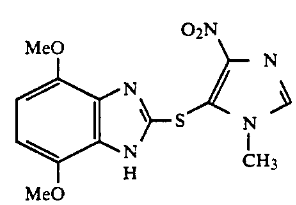
(6)
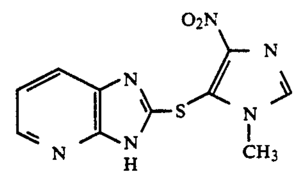
(7)
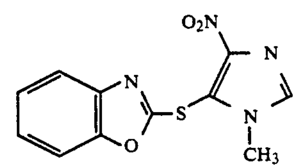
(8)
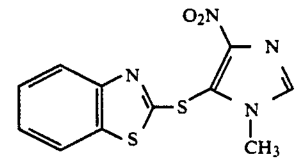
(9)

-continued
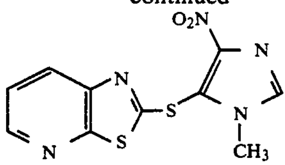
(10)
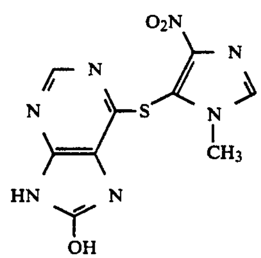
(11)
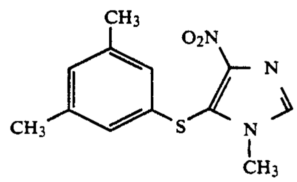
(12)
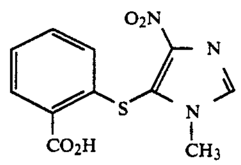
(13)
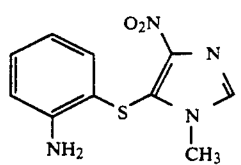
(14)
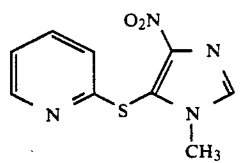
(15)
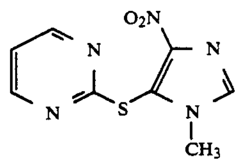
(16)
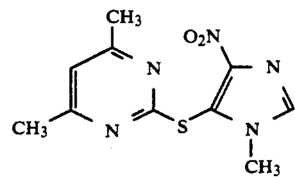
(17)
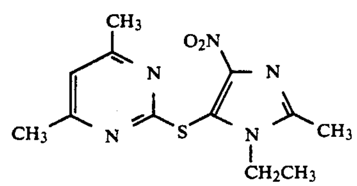
(18)
-continued
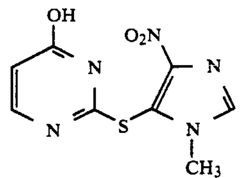
(19)
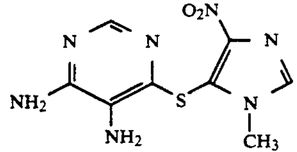
(20)
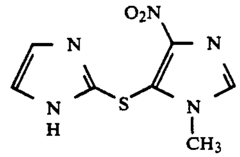
(21)
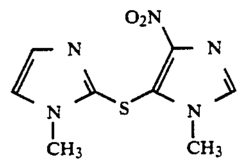
(22)
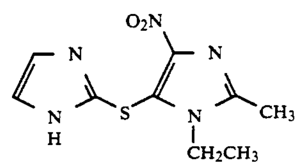
(23)
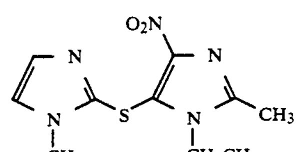
(24)
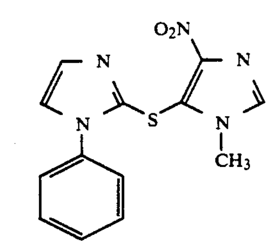
(25)
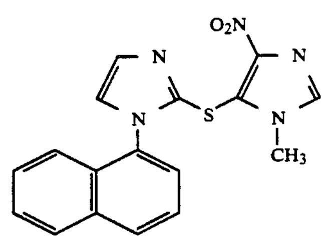
(26)
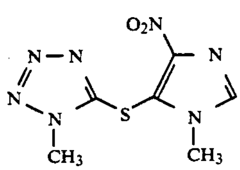
(27)

-continued
(28)
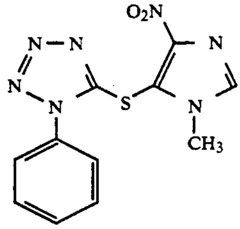
(29)
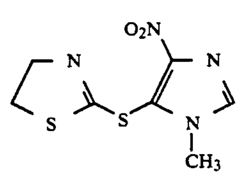
(30)
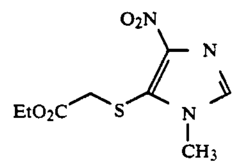
(31)
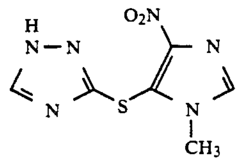
(32)
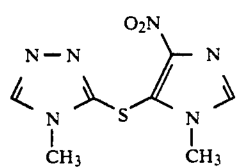
(33)
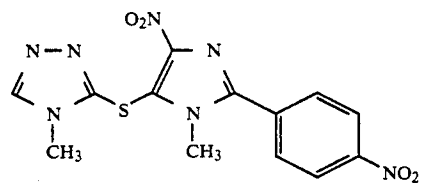
(34)
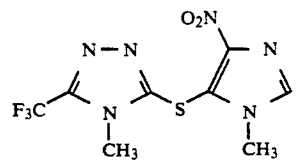
(35)
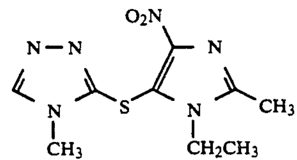
(36)
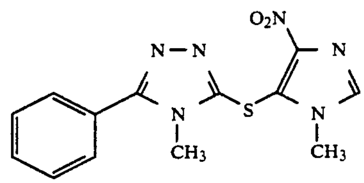
-continued
(37)
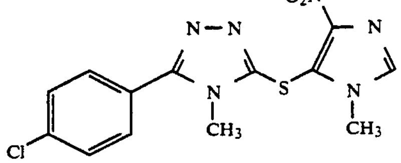
(38)
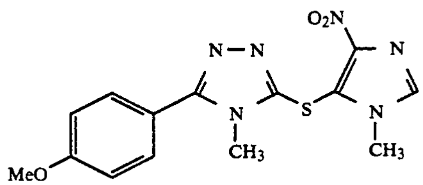
(39)
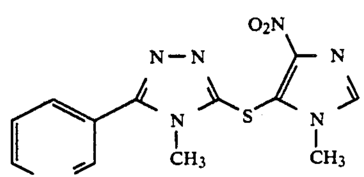
(40)
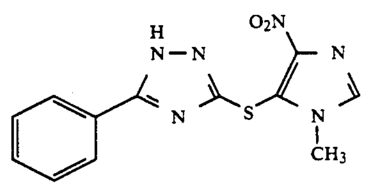
(41)
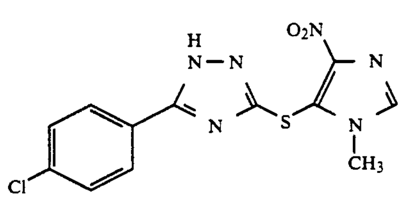
(42)
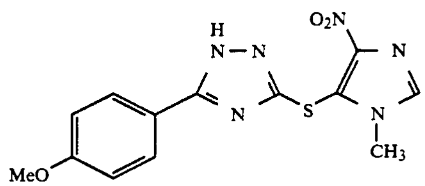
(43)
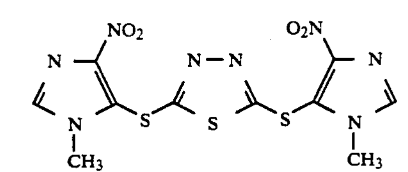
Some of the compounds, as referred to above are previously unknown.
Therefore, according to a further aspect of the invention there are provided compounds comprising the following formula:
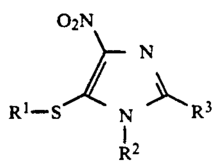

wherein the molecular groups $R^1$, $R^2$, and $R^3$ are defined as one of the following:

1. $R^1$ is defined as the following:

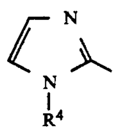

in which
$R^4$ is hydrogen or methyl;
$R^2$ is ethyl; and
$R^3$ is methyl OR
$R^2$ is methyl and $R^3$ is hydrogen; and
$R^4$ is phenyl or 1-naphthyl OR 2. $R^1$ is defined as the following:

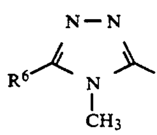

in which
$R^2$,$R^3$, and $R^5$ are one of the following combinations:
$R^2$ is methyl, $R^3$ is 4-nitrophenyl, and $R^5$ is hydrogen; or
$R^2$ is methyl, $R^3$ is hydrogen, and $R^5$ is trifluoromethyl; or
$R^2$ is ethyl, $R^3$ is methyl, and $R^5$ is hydrogen; or
$R^2$ is methyl, $R^3$ is hydrogen, and $R^5$ is phenyl; or
$R^2$ is methyl, $R^3$ is hydrogen, and $R^5$ is 4-chlorophenyl; or
$R^2$ is methyl, $R^3$ is hydrogen, and $R^5$ is 4-methocyphenyl; or
$R^2$ is methyl, $R^3$ is hydrogen, and $R^5$ is 3-pyridyl OR 3. $R^1$ is defined as the following:

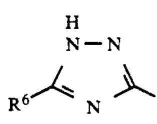

in which
$R^2$ is methyl; and
$R^3$ is hydrogen; and
$R^6$ is hydrogen or phenyl or 4-chlorophenyl o 4-methoxyphenyl OR 4. $R^1$ is defined as the following:

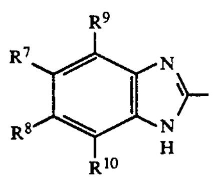

in which
$R^2$ is methyl; and
$R^3$ is hydrogen, and
$R^7$, $R^8$, $R^9$, $R^{10}$ are one of the following combinations:
$R^8$, $R^9$, $R^{10}$ are all hydrogen and $R^7$ is methyl; or
$R^8$, $R^9$, $R^{10}$ are all hydrogen and $R^7$ is a nitro group; or
$R^9$ and $R^{10}$ are both hydrogen, $R^7$ is fluorine, and $R^8$ is chlorine; or
$R^9$ and $R^{10}$ are both hydrogen, and $R^7$ and $R^8$ are both methoxy groups; or
$R^7$ and $R^8$ are both hydrogen and $R^9$ and $R^{10}$ are both methoxy groups OR 5. $R^1$ is defined as the following:

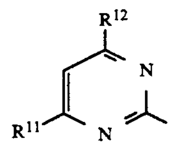

in which
$R^2$ is methyl; and
$R^3$ is hydrogen; and
$R^{11}$,$R^{12}$ and X are defined as one of the following combinations:
$R^{11}$ and $R^{12}$ are both hydrogen, and X is C—H; or
$R^{11}$ is a hydroxy group, $R^{12}$ is hydrogen, and X is nitrogen OR
$R^2$ is ethyl; and
$R^3$, $R^{11}$ and $R^{12}$ are all methyl; and
X is nitrogen OR 6. $R^1$ is defined as the following:

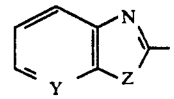

in which
$R^2$ is methyl; and
$R^3$ is hydrogen; and
Y and Z are defined as one of the following combinations:
Y is C—H and Z is oxygen; or
Y is nitrogen and Z is sulphur; or
Y is nitrogen and Z is N—H OR 7. $R^1$ is defined as the following:

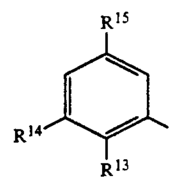

in which
$R^2$ is methyl; and
$R^3$ is hydrogen; and
$R^{13}$,$R^{14}$, and $R^{15}$ are defined in either of the following combinations:
$R^{13}$ is hydrogen, and $R^{14}$ and $R^{15}$ are both methyl; or
$R^{13}$ is carboxyl, and $R^{14}$ and $R^{15}$ are both hydrogen OR 8. $R^1$ is defined as the following:

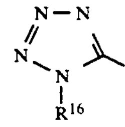

in which $R^2$ is methyl; and $R^3$ is hydrogen; and $R^{16}$ is methyl or phenyl OR 9. $R^1$ is defined as the following:

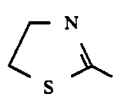

OR

10. $R^1$ is defined as the following:

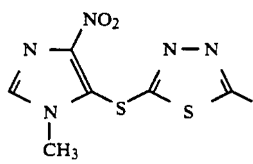

OR

11. $R^1$ is defined as the following:

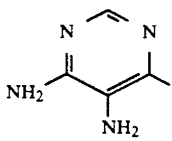

Referring now to Reaction Scheme 1, azathioprine I was originally designed as a "pro-drug" for 6-mercaptopurine II, to which it is rapidly converted by red blood cells. 6-mercaptopurine II has immunosupressive properties, but the mechanism of its action is unclear.

REACTION SCHEME 1

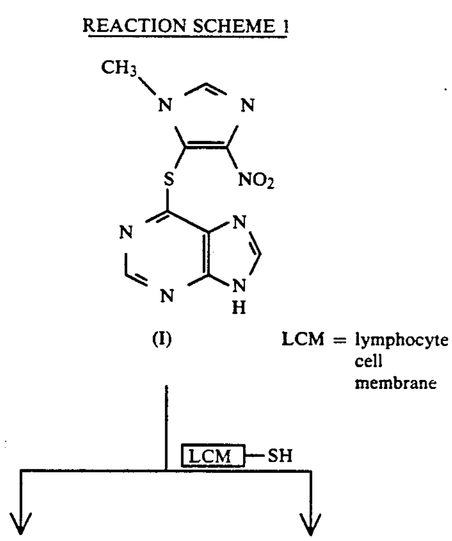

-continued

REACTION SCHEME 1

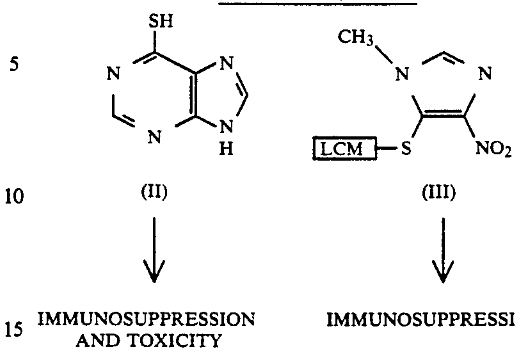

It would appear that the immunosuppressive action of azathioprine I is due not solely to prior conversion of 6-mercaptopurine II in the body, but to the immunosuppressive action of azathioprine I itself. The mechanism of action of azathioprine I differs from that of 6-mercaptopurine II. There is strong evidence to suggest that 6-mercaptopurine II is converted in vivo into a nucleotide metabolite that is associated with bone marrow toxicity. There is no evidence to suggest that metabolites derived from the 1-methyl-4-nitroimidazole moiety of azathioprine give rise to toxicity.

It is thought L-hat azathioprine I alkylates thiol groups in the lymphocyte cell membrane, most probably by a process of addition-elimination with the consequent release of 6-mercaotopurine II. It is further supposed that the alkylation of the lymphocyte results in immunosuppression, whilst the 6-mercaptopurine II gives rise, as stated above, via its nucleotide metabolite, to bone marrow toxicity. Support for this hypothesis is provided by the fact that lymphocyte cell membranes are richly endowed with thiol groups, and by the known propensity of azathioprine to react with thiols both in vitro and in vivo.

5-(1-alkyl-4-nitroimidazole) derivatives VI of relatively non toxic alkyl thiols or aryl thiols V are therefore suitable candidates for evaluation as good, relatively non toxic immunosuppressive agents, as 5 shown in Reaction Scheme 2.

REACTION SCHEME 2

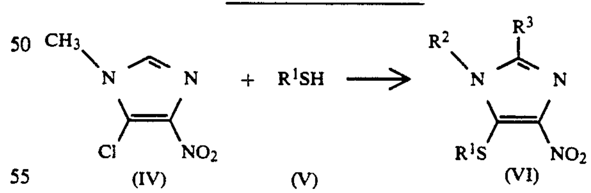

$R^1$ = alkyl, aryl, or heterocyclic
$R^2$ = Me or Et
$R^3$ = H or Me

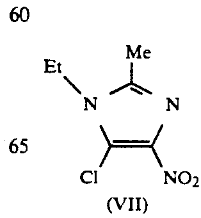

-continued
REACTION SCHEME 2

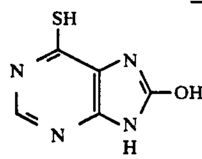

(VIII)

Examples of immunosuppressive agents of this kind are shown previously in examples 1-43. It is not intended that the invention be limited to these illustrative examples.

Compounds 1 to 17, 19 to 22, 25 to 32, 34 and 36 to 43 may be synthesised, for example, by reaction of 5-chloro-1-methyl-4-nitroimidazole 1V with the appropriate thiol V and potassium carbonate in a suitable solvent such as, for example, tetrahydrofuran, dimethylformamide, or water. Compounds 18, 23, 24 and 35 may be synthesised, for example from 5-chloro-1-ethyl-2-methyl-4-nitroimidazole VII and the appropriate thiol under suitable conditions, such as, for example, in acetone in the presence of potassium carbonate.

Sixteen of these compounds were screened for immunosuppressive activity by means of the human mixed lymphocyte reaction, which is well known and need not be further described here, the results of which are shown in Table 1.

TABLE 1

| Compound | Concentration of Solution (μM) | % Inhibition of $^3$M-Thymidine |
|---|---|---|
| I (azathioprine) | 25 | 79 |
| 21 | 10 | 89 |
| 22 | 10 | 82 |
| 32 | 25 | 98 |
| 1 | 36 | 98 |
| 2 | 25 | 86 |
| 4 | 50 | 59 |
| 5 | 25 | 94 |
| 6 | 25 | 41 |
| 15 | 25 | 76 |
| 16 | 25 | 47 |
| 19 | 25 | 29 |
| 18 | 25 | 47 |
| 8 | 25 | 87 |
| 9 | 25 | 27 |
| 13 | 25 | 34 |
| 30 | 25 | 65 |

The individual figures in the right hand column of the above table are directly proportioned to immunosuppressive activity.

As can be seen from Table 1 all of the compounds screened for immunosuppressive activity displayed significant immunosuppression, and six were substantially more active than azathioprine at the same concentration (25 μM).

Table 2 shows the measure of the immunosuppressive activity and toxicity of compounds 21,22,32, and 11.

TABLE 2

| Compound | Immunosuppressive activity[a] $ED_{50}$ | Toxicity[b] $LD_{25}$ | Therapeutic index $ED_{50}/LD_{25}$ |
|---|---|---|---|
| I (azathioprine) | 7.9 | 42.5 | 5.38 |
| 21 | 2.8 | c | vh |
| 22 | 3.15 | d | vh |
| 32 | 1.6 | | |
| 11 | 24.0 | e | vh |

[a] $ED_{50}$ = concentration (μM) which brings about 50% inhibition of $^3$H-thymidine incorporation in the human mixed lymphocyte reaction: lower figures indicate increased reactivity
[b] $LD_{25}$ = concentration (μM) at which 25% of the cells are killed: lower figures indicate increased toxicity
[c] No $LD_{25}$ because only 19% of cells killed at 100 μM
[d] No $LD_{25}$ because only 15% of cells killed at 215 μM
[e] No $LD_{25}$ because only 16% of cells killed at 25 μM
(For c, d and e these are maximum vaules: no more cells were killed at higher concentrations)
vh very high Referring now to Table 2, imidazole derivatives 21 and 22 and the triazole derivative 32 are shown to be substantially more immunosuppressive than azathiourine and also considerably less toxic to lymphocytes. Therapeutic indices for these compounds are therefore at least an order of magnitude greater than for azathioprine.

The compound 11 in which the 6-mercaptopurine moiety of azathioprine is replaced by 8-hydroxy-6-mercaptopurine moiety, is less immunosuppressive than azathioprine according to the mixed human lymphocyte reaction, as is shown in Table 2, but is much less toxic to the lymphocytes. The therapeutic index of compound is therefore much greater than that of azathioprine, according to these tests. The significance of this result resides in the fact that 8-hydroxy-6-mercaptopurine VIII is known to be a non toxic metabolite of azathioprine, and its metabolic fate is known.

Compound 32 showed pronounced immunosuppressive activity in vivo. It was tested in CBA mice transplanted with skin from Balb/c mice, according to the skin grafting technique described by Billingham and Medawar (J.Exp. Biol, 28, 385-405 (1951). The effect compound 32 had on skin graft survival was compared with a control of saline, and with the standard immunosuppressive agent azathioprine. All drugs were injected into the peritoneum starting three hours before surgery and then daily until the graft had fully rejected. Mice were placed in groups at random, and rejection of the graft was evaluated by visual inspection by an independent observer. The results are recorded in Table 3.

TABLE 3

| Treatment | Number of mice | Dosage* (mg/Kg/day) | Graft survival (Mean ± SEM days) |
|---|---|---|---|
| Control | 28 | NA | 12.5 ± 0.4 |
| Compound 32 | 24 | 45 | 14.2 ± 0.4 |
| athloprine | 29 | 52 | 12.4 ± 0.3 |

*Compound 32 and azathioprine were administered in equimolar amounts

The prolongation of graft survival caused by compound 32 (1.7 days) compared to a saline control is significant statistically ($p=5.9\times10^{-3}$). Similarly, the prolongation of graft survival caused by compound 32 (1.8 days) compared to azathioprine is also highly significant ($p=2.84\times10^{-3}$).

It is to be understood that the above described examples are for illustration only and that many modifications and variations can be made within the scope of the invention.

We claim:

1. A method of suppressing the immune system of a human comprising administering to a person requiring same an effective amount of a compound of the formula

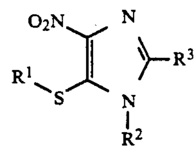

in which $R^1$ is a five member heterocyclic ring system having 2, 3, or 4 nitrogens, or 2 nitrogens and 1 sulfur or 1 nitrogen and 1 sulfur, which may be optionally substituted or unsustituted; $R^2$ is hydrogen, lower alkyl or aryl; and $R^3$ is hydrogen, lower alkyl, aryl and nitroaryl, wherein aryl is phenyl or napthyl.

2. In the method of claim 1, $R^2$ comprising hydrogen, methyl, ethyl or propyl; and $R^3$ is hydrogen, methyl or 4-nitrophenyl.

3. In the method of claim 1, said immunosupressive agent having the formula

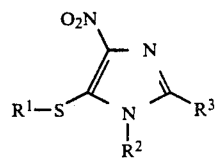

wherein $R^2$ is hydrogen, methyl, ethyl or propyl and $R^3$ is hydrogen methyl or 4-nitrophenyl, and wherein $R^1$ is one of the following (i)

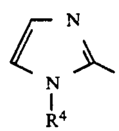

in which $R^4$ is hydrogen or methyl or ethyl or propyl or phenyl or 1-phenyl OR (ii)

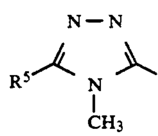

in which $R^5$ is hydrogen or trifluoromethyl or phenyl or 4-chlorophenyl or 4-methoxyphenyl OR (iii)

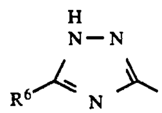

in which $R^6$ is hydrogen or phenyl or chlorophenyl or 4-methoxyphenyl OR (iv)

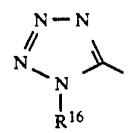

in which $R^{16}$ is alkyl or aryl OR (v)

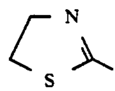

(vi)

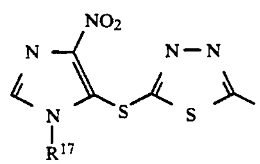

in which $R^{17}$ is alkyl or aryl.

4. A method of suppressing the immune system of a human comprising administering to a person requiring same an effective amount of a compound of the formula:

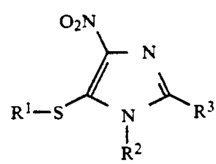

wherein the molecular groups $R^1$, $R^2$ and $R^3$ are defined as one of the following:

(i) $R^1$ is defined as the following;

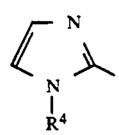

in which $R^4$ is hydrogen or methyl;
$R^2$ is ethyl; and
$R^3$ is methyl OR
$R^2$ is methyl and $R^3$ is hydrogen; and
$R^4$ is phenyl or 1-naphthyl OR (ii) $R^1$ is defined as the following:

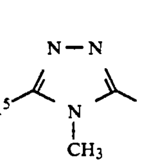

$R^2$,$R^3$, and $R^5$ are one of the following combinations:
$R^2$ is methyl, $R^3$ is 4-nitrophenyl, and $R^5$ is hydrogen; or $R^2$ is methyl, $R^3$ is hydrogen, and $R^5$ is trifluoromethyl; or $R^2$ is ethyl, $R^3$ is methyl, and $R^5$ is hydrogen; or $R^2$ is methyl, $R^3$ is hydrogen, and $R^5$ is phenyl; or $R^2$ is methyl, $R^3$ is hydrogen, and $R^5$ is 4-chlorophenyl; or $R^2$ is methyl, $R^3$ is hydrogen, and $R^5$ is 4-methoxyphenyl; or $R^2$ is methyl, $R^3$ is hydrogen, and $R^5$ is 3-pyridyl OR (iii) $R^1$ is defined as the following:

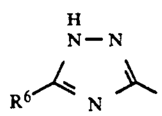

in which $R^2$ is methyl; and $R^3$ is hydrogen; and $R^6$ is phenyl or 4-chlorophenyl or 4-methoxyphenyl OR (iv) $R^1$ is defined as the following:

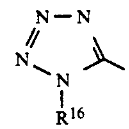

in which $R^2$ is methyl; and $R^3$ is hydrogen; and $R^{16}$ is methyl or phenyl OR (v) $R^1$ is defined as the following:

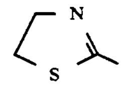

OR (vi) $R^1$ is defined as the following:

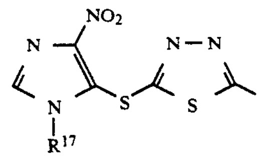

* * * * *